(12) United States Patent
Sabatini et al.

(10) Patent No.: US 9,999,352 B2
(45) Date of Patent: Jun. 19, 2018

(54) SYSTEM AND METHOD FOR DETERMINING A HYDRATION LEVEL OF A TISSUE REGION

(71) Applicant: General Electric Company, Schenectady, NY (US)

(72) Inventors: James Enrico Sabatini, Scotia, NY (US); Jeffrey Michael Ashe, Gloversville, NY (US); Xiaohui Chen, Schenectady, NY (US); Tzu-Jen Kao, Watervliet, NY (US)

(73) Assignee: General Electric Company, Schenectady (*) Notice: Subject to any disclaimer, the term of this patent is extended or adjusted under 35 U.S.C. 154(b) by 1184 days.

(21) Appl. No.: 14/039,497

(22) Filed: Sep. 27, 2013

(65) Prior Publication Data

US 2015/0094548 A1    Apr. 2, 2015

(51) Int. Cl.
*A61B 5/00* (2006.01)
*A61B 5/053* (2006.01)

(52) U.S. Cl.
CPC .......... *A61B 5/0053* (2013.01); *A61B 5/0537* (2013.01); *A61B 5/4878* (2013.01); *A61B 5/4875* (2013.01)

(58) Field of Classification Search
None
See application file for complete search history.

(56) References Cited

U.S. PATENT DOCUMENTS

| | | | |
|---|---|---|---|
| 5,807,272 A | 9/1998 | Kun et al. | |
| 7,645,243 B2 | 1/2010 | Lindahl | |
| 8,208,985 B2 | 6/2012 | Kim et al. | |
| 8,374,688 B2 | 2/2013 | Libbus et al. | |
| 2001/0037068 A1* | 11/2001 | Goto ................. | A61B 5/02116 600/485 |
| 2002/0188206 A1 | 12/2002 | Davis et al. | |

(Continued)

FOREIGN PATENT DOCUMENTS

| | | |
|---|---|---|
| EP | 2662020 A1 | 11/2013 |
| WO | 1997039792 A1 | 10/1997 |

OTHER PUBLICATIONS

The International Search Report and Written Opinion issued in connection with corresponding WO Patent Application No. PCT/US2014/058038 dated Dec. 4, 2014.

(Continued)

*Primary Examiner* — Jacqueline Cheng
*Assistant Examiner* — Jairo Portillo
(74) *Attorney, Agent, or Firm* — GE Global Patent Operation; John Darling (57) ABSTRACT

In accordance with one aspect of the present technique, a method is disclosed. The method includes applying a mechanical perturbation to a tissue region using a displacement device. The method further includes calculating a compression impedance of the tissue region in response to applying the mechanical perturbation. The method further includes retracting the displacement device and calculating a retraction impedance of the tissue region in response to retracting the displacement device. The method also includes determining a hydration level of the tissue region based on at least one of the compression impedance and the retraction impedances.

20 Claims, 8 Drawing Sheets

(56) References Cited

U.S. PATENT DOCUMENTS

| | | | |
|---|---|---|---|
| 2003/0120170 A1* | 6/2003 | Zhu | A61B 5/0537 600/547 |
| 2005/0131310 A1* | 6/2005 | Freund | A61B 5/02233 600/499 |
| 2006/0264775 A1 | 11/2006 | Mills et al. | |
| 2010/0114204 A1* | 5/2010 | Burnes | A61N 1/36146 607/4 |
| 2010/0261985 A1* | 10/2010 | Cohen-Solal | A61B 5/0055 600/306 |
| 2012/0157798 A1* | 6/2012 | Averina | A61B 5/0205 600/301 |
| 2013/0197340 A1 | 8/2013 | Sanders et al. | |

OTHER PUBLICATIONS

"A Dynamic Compression System for Improving Ulcer Healing: Design of a Sensing Garment" dated Aug. 20, 2008.

Gerth et al., "A Computer-Based Bioelectrical Impedance Spectroscopic System for Noninvasive Assessment of Compartmental Fluid Redistribution", Third Annual IEEE Symposium on Computer-Based Medical Systems, 1990, pp. 446-453.

Abboud et al., "Monitoring of Peripheral Edema using Electrical Bioimpedance Measurements", Engineering in Medicine and Biology Society, 1995., IEEE 17th Annual Conference (vol. 1), pp. 641-642.

Walker et al., "Modelling the Electrical Properties of Bladder Tissue—Quantifying Impedance Changes due to Inflammation and Oedema", Institute of Physics Publishing, Physiological Measurement, vol. 26, 2005, pp. 251-268.

Correa et al., "Electrical Bioimpedance Readings Increase with Higher Pressure Applied to the Measuring Probe", Institute of Physics Publishing, Physiological Measurement, vol. 26, 2005, pp. S39-S47.

* cited by examiner

SYSTEM AND METHOD FOR DETERMINING A HYDRATION LEVEL OF A TISSUE REGION

BACKGROUND

The subject matter disclosed herein generally relates to determining a hydration level of a tissue region. More specifically, the subject matter relates to systems and methods for determining an edema stage or a dehydration stage of a tissue region based on electrical impedance measurements of the tissue region.

Primary care physicians and specialist doctors combine tissue hydration levels (e.g., edema stage) with other medical data to monitor progression in the diagnosis and management of diseases, for example, toxemia in pregnancies, heart failures, kidney diseases, liver cirrhosis, and the like. Currently, to determine an edema stage of a user's tissue region, physicians create a pit by applying finger pressure on the tissue region and observe the depth of the pit and/or the time for the tissue region to return to the normal state. Such edema staging methods cause numerous problems as they are qualitative and are dependent on the perception of the physicians.

Thus, there is a need for an enhanced system and method for determining a hydration level of a tissue region.

BRIEF DESCRIPTION

In accordance with one embodiment, a method is disclosed. The method includes applying a mechanical perturbation to a tissue region using a displacement device. The method further includes calculating a compression impedance of the tissue region in response to applying the mechanical perturbation. The method further includes retracting the displacement device and calculating a retraction impedance of the tissue region in response to retracting the displacement device. The method also includes determining a hydration level of the tissue region based on at least one of the compression impedance and the retraction impedance.

In accordance with another embodiment, a system is disclosed. The system includes a displacement module for applying a mechanical perturbation to a tissue region using a displacement device and retracting the displacement device. The system further includes an impedance module for calculating a compression impedance of the tissue region in response to applying the mechanical perturbation and a retraction impedance of the tissue region in response to retracting the displacement device. The system further includes a staging module for determining a hydration level of the tissue region based on at least one of the compression impedance and the retraction impedance.

In accordance with yet another embodiment, a computer program product encoding instructions is disclosed. The instructions when executed by a processor, causes the processor to apply a mechanical perturbation to the tissue region using a displacement device. The instructions further cause the processor to calculate a compression impedance of the tissue region in response to applying the mechanical perturbation. The instructions further cause the processor to retract the displacement device and calculate a retraction impedance of the tissue region in response to retracting the displacement device. The instructions further cause the processor to determine a hydration level of the tissue region based on at least one of the compression impedance and the retraction impedance.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

In the following specification and the claims, reference will be made to a number of terms, which shall be defined to have the following meanings.

The singular forms "a", "an", and "the" include plural references unless the context clearly dictates otherwise.

As used herein, the term "non-transitory computer-readable media" is intended to be representative of any tangible computer-based device implemented in any method or technology for short-term and long-term storage of information, such as computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

As used herein, the terms "software" and "firmware" are interchangeable, and may include any computer program stored in memory for execution by devices that include, without limitation, mobile devices, clusters, personal computers, workstations, clients, and servers.

As used herein, the term "computer" and related terms, e.g., "computing device", are not limited to integrated circuits referred to in the art as a computer, but broadly refers to at least one microcontroller, microcomputer, programmable logic controller (PLC), application specific integrated circuit, and other programmable circuits, and these terms are used interchangeably herein.

Approximating language, as used herein throughout the description and claims, may be applied to modify any quantitative representation that could permissibly vary without resulting in a change in the basic function to which it is related. Accordingly, a value modified by a term or terms, such as "about" and "substantially", are not limited to the precise value specified. In at least some instances, the approximating language may correspond to the precision of an instrument for measuring the value. Here and throughout the specification and claims, range limitations may be combined and/or inter-changed, such ranges are identified and include all the sub-ranges contained therein unless context or language indicates otherwise.

Figure 1:
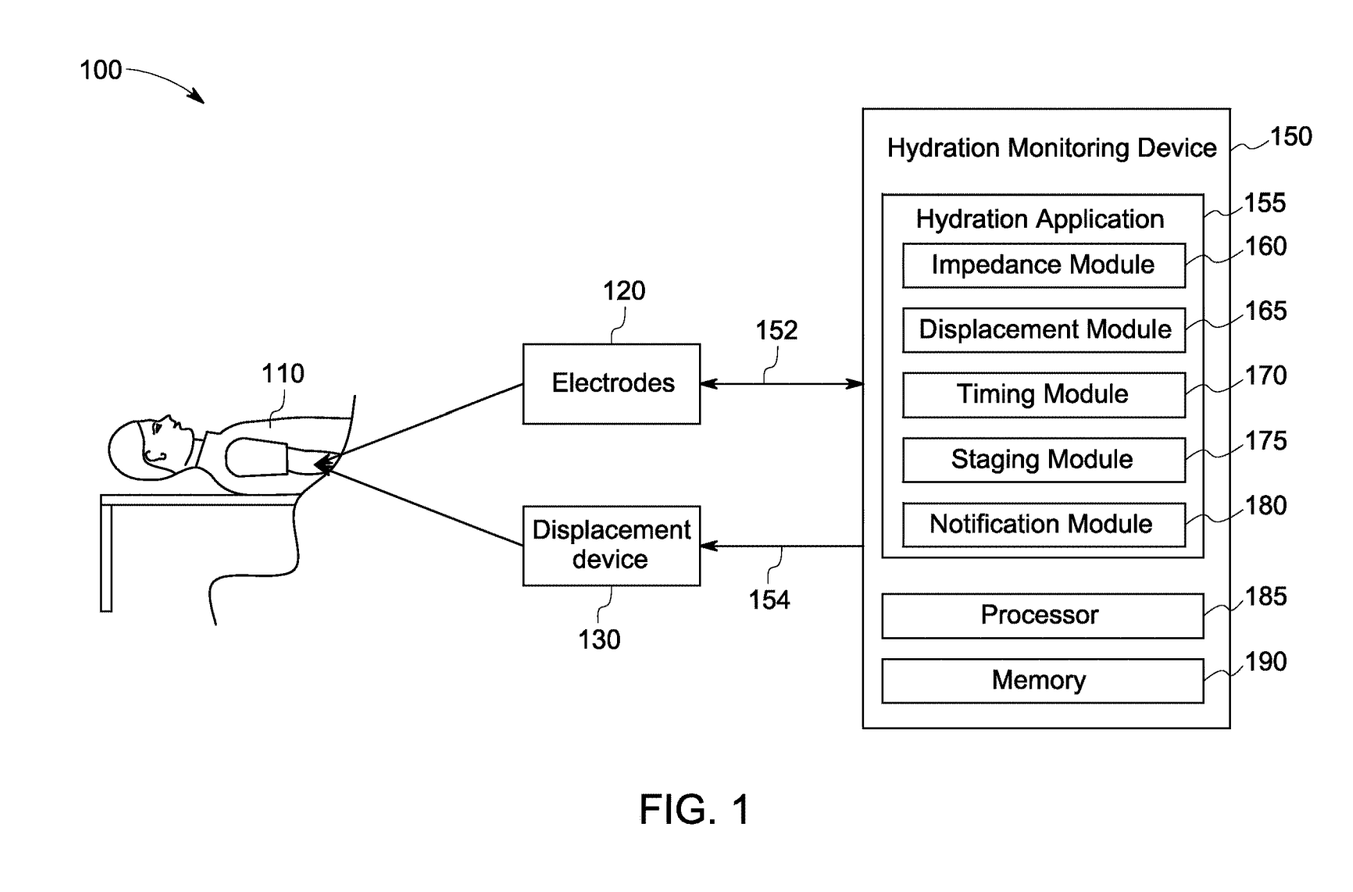
FIG. 1 is a block diagram illustrating a system for determining a hydration level of a tissue region according to one embodiment.

A system and method for determining a hydration level of a tissue region is described herein. FIG. 1 illustrates a block diagram of a system 100 for determining a hydration level of a user 110 according to one embodiment. The illustrated system 100 includes a plurality of electrodes 120, a displacement device 130, and a hydration monitoring device 150. In the illustrated embodiment, the plurality of electrodes 120, the displacement device 130, and the hydration monitoring device 150 are used to determine the hydration level of a tissue region (e.g., tissue of the leg, hand, face, and the like) of the user 110 (e.g., a patient in a hospital, a remote patient at home, an athlete monitoring fitness levels, and the like).

The plurality of electrodes 120 are any type of electrical conductors used to make contact with a non-metallic part (i.e., the tissue region) of an electrical circuit. The plurality of electrodes 120 are configured to apply and measure electrical current/voltage from the tissue region. In the illustrated embodiment, the plurality of electrodes 120 are coupled to the hydration monitoring device 150 via electrically conductive cables 152. The plurality of electrodes 120 are configured to receive a signal from the hydration monitoring device 150 and apply and measure electrical current/voltage from the tissue region. For example, the plurality electrodes 120 receive the signal from an electrical circuit/instrument (not shown) included in the hydration monitoring device 150. In one embodiment, the plurality of electrodes 120 includes a pair of injection electrodes to apply the electrical current to the tissue region. In such an embodiment, the plurality of electrodes 120 also include a pair of measurement electrodes configured to measure the electric voltage caused due to the electric current applied by the injection electrodes. The pair of measurement electrodes is placed in close proximity to the pair of injection electrodes on the tissue region. Although the plurality of electrodes 120 are described according to one embodiment as including two separate pairs of electrodes, in other embodiments, the plurality of electrodes 120 may include a single pair of electrodes configured for both applying electric current and measuring electric voltage.

The displacement device 130 is any device for applying a mechanical perturbation (i.e., an indentation or a depression) on the tissue region. In one embodiment, the displacement device 130 may be a blood pressure cuff for applying the mechanical perturbation. In another embodiment, the displacement device 130 may be a plunging device that applies the mechanical perturbation. In the illustrated embodiment, the displacement device 130 is coupled to the hydration monitoring device 150 via a signal line 154. The displacement device 130 is configured to receive a communication from the hydration monitoring device 150 and apply a mechanical perturbation to the tissue region by, for example, pushing into the tissue region. For example, the displacement device 130 receives the communication from a mechatronic system (not shown) included in the hydration monitoring device 150. The application of the mechanical perturbation may be controlled by the amount of force applied by the displacement device 130 on the tissue region or the amount of displacement caused to the tissue region. In one embodiment, the displacement device 130 is positioned such that the mechanical perturbation is applied in-between the placement of the plurality of electrodes 120 on the tissue region. The displacement device 130 is further configured to receive another communication from the hydration monitoring device 150 to reverse the mechanical perturbation applied on the tissue region. The displacement device 130 retracts from the tissue region in response to the communication to reverse the mechanical perturbation.

The hydration monitoring device 150 may be any device used for monitoring a hydration level of a tissue region. In the illustrated embodiment, the hydration monitoring device 150 includes a hydration application 155, a processor 185, and a memory 190. The hydration application 155 includes an impedance module 160, a displacement module 165, a timing module 170, a staging module 175, and a notification module 180. The plurality of modules of the hydration application 155, the processor 185, and the memory 190 are coupled to a bus (not shown) for communication with each other.

The processor 185 may include at least one arithmetic logic unit, microprocessor, general purpose controller or other processor arrays to perform computations, and/or retrieve data stored on the memory 190. In another embodiment, the processor 185 is a multiple core processor. The processor 185 processes data signals and may include various computing architectures including a complex instruction set computer (CISC) architecture, a reduced instruction set computer (RISC) architecture, or an architecture implementing a combination of instruction sets. The processing capability of the processor 185 in one embodiment may be limited to supporting the retrieval of data and transmission of data. The processing capability of the processor 185 in another embodiment may also include performing more complex tasks, including various types of feature extraction, modulating, encoding, multiplexing, and the like. In other embodiments, other type of processors, operating systems, and physical configurations are also envisioned.

The memory 190 may be a non-transitory storage medium. For example, the memory 190 may be a dynamic random access memory (DRAM) device, a baseline random access memory (SRAM) device, flash memory or other memory devices. In one embodiment, the memory 190 also includes a non-volatile memory or similar permanent storage device, and media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices.

The memory 190 stores data that is required for the hydration application 155 to perform associated functions.

In one embodiment, the memory 190 stores the modules (for example, the impedance module 160, the displacement module 165, and the like) of the hydration application 155. In another embodiment, the memory 190 stores threshold values that are defined by, for example, an administrator (e.g., a doctor) of the hydration monitoring device 150. The threshold values are described below in further detail with reference to the impedance module 160.

The impedance module 160 includes codes and routines for calculating an impedance of the tissue region. In one embodiment, the impedance module 160 includes a set of instructions executable by the processor 185 to provide the functionality for calculating the impedance of the tissue region. In another embodiment, the impedance module 160 is stored in the memory 190 and is accessible and executable by the processor 185. In either embodiment, the impedance module 160 is adapted for communication and cooperation with the processor 185 and other modules of the hydration application 155.

The impedance module 160 is configured to apply electric current to the tissue region via the plurality of electrodes 120 (i.e., a pair of injection electrodes). The impedance module 160 is also configured to measure the electric voltage across the tissue region generated due to the applied electric current, via the plurality of electrodes 120 (i.e., the pair of measurement electrodes). In one embodiment, the impedance module 160 may be coupled with an electrical system/instrument (not shown). In such an embodiment, the impedance module 160 sends an instruction to the electrical system to apply the electrical current into the tissue region and measure the electrical voltage of the tissue region via the plurality of electrodes 120. The impedance module 160 then calculates the impedance of the tissue region based on the applied electric current and the measured electric voltage. In one embodiment, the impedance module 160 calculates the impedance as the measured electric voltage divided by the applied electric current.

In one embodiment, the impedance module 160 applies the electrical current and receives the electrical voltage measurements continuously and calculates the impedance of the tissue region in real-time. For the purpose of clarity and convenience, the impedance of the tissue region, prior to applying any mechanical perturbation to the tissue region, is referred to herein, as the "baseline impedance." The impedance module 160 sends a message to the displacement module 165 in response to calculating the baseline impedance of the tissue region.

Similarly, for the purpose of clarity and convenience, the impedance of the tissue region corresponding to the application of a mechanical perturbation is referred to herein, as the "compression impedance" (CI). The impedance module 160 is further configured to calculate a rate of change of CI. The rate of change of CI may be determined using a linear function, an exponential function, a quadratic function, and the like. The impedance module 160 then sends the rate of change of CI to the staging module 175. In one embodiment, the impedance module 160 determines whether the CI has reached a steady state CI, after the application of the mechanical perturbation. In such an embodiment, the impedance module 160 determines whether the rate of change of CI is within a stabilization threshold range. The stabilization threshold range (e.g., −1 ohms/sec to +1 ohms/sec, −0.5 milliohms/sec to +0.5 milliohms/sec) is defined by, for example, an administrator of the hydration monitoring device 150. The impedance module 160 calculates a CI change in response to determining that the rate of change of CI is within the stabilization threshold range. Specifically, the impedance module 160 calculates the CI change as the difference between the baseline impedance and the steady state CI. The impedance module 160 sends the CI change to the staging module 175.

In another embodiment, the impedance module 160 determines whether the rate of change of CI is less than a CI threshold. The CI threshold is defined by, for example, an administrator of the hydration monitoring device 150. The impedance module 160 determines a fast CI change in response to determining that the rate of change of CI is less than the CI threshold. Specifically, the impedance module 160 calculates the fast CI change as the difference between the baseline impedance and the impedance value of the tissue region in response to determining that the rate of change of CI is less than the CI threshold. In such an embodiment, the impedance module 160 further determines a slow CI change as the difference between the steady state CI and the impedance value of the tissue region in response to determining that the rate of change of CI is less than the CI threshold. Typically, in response to the application of the mechanical perturbation, the fast CI change is caused due to the compression of, for example, the skin in the tissue region and the slow CI change is caused due to the compression of fluid in the tissue region. The impedance module 160 sends the slow CI change and the fast CI change to the staging module 175.

For the purpose of clarity and convenience, the impedance of the tissue region corresponding to the retraction of the displacement device from the tissue region is referred to herein, as the "retraction impedance" (RI). The impedance module 160 is configured to calculate a rate of change of RI and send the rate of change of RI to the staging module 175. In one embodiment, the impedance module 160 determines whether the RI has reached a steady state RI after the retraction of the displacement device 130 from the tissue region. In such an embodiment, the impedance module 160 determines whether the rate of change of RI is within the stabilization threshold range. The impedance module 160 calculates a RI change in response to determining that the rate of change of RI is within the stabilization threshold range. The impedance module 160 calculates the RI change as the difference between the steady state CI and the steady state RI. The impedance module 160 sends the RI change to the staging module 175.

In another embodiment, the impedance module 160 determines whether the rate of change of RI is less than a RI threshold. The RI threshold is defined by, for example, an administrator of the hydration monitoring device 150. The impedance module 160 calculates a fast RI change in response to determining that the rate of change of RI is less than the RI threshold. Specifically, the impedance module 160 calculates the fast RI change as the difference between the steady state CI and the impedance value of the tissue region in response to determining that the rate of change of RI is less than the RI threshold. In such an embodiment, the impedance module 160 further calculates a slow RI change as the difference between the steady state RI and the impedance value of the tissue region in response to determining that the rate of change of RI is less than the RI threshold. Typically, the fast RI change is caused due to the expansion of, for example, the skin in the tissue region and the slow RI change is caused due to the expansion of the fluid in the tissue region. The impedance module 160 sends the slow RI change and the fast RI change to the staging module 175.

The displacement module 165 includes codes and routines for applying mechanical perturbation to the tissue region and retracting the displacement device 130 from the tissue region. In one embodiment, the displacement module 165 includes a set of instructions executable by the processor 185 to provide the functionality for applying mechanical perturbation to the tissue region and retracting the displacement device 130 from the tissue region. In another embodiment, the displacement module 165 is stored in the memory 190 and accessible and executable by the processor 185. In either embodiment, the displacement module 165 is adapted for communication and cooperation with the processor 185 and other modules of the hydration application 155.

The displacement module 165 is configured to communicate with the displacement device 130 to apply a mechanical perturbation to the tissue region. In one embodiment, the displacement module 165 may be coupled with a mechatronic system (not shown). In such an embodiment, the displacement module 165 sends an instruction to the displacement device 130 to apply the mechanical perturbation via the mechatronic system. The displacement module 165 applies the mechanical perturbation based on a pre-determined force or a pre-determined displacement of the tissue region. For example, the displacement module 165 instructs the mechatronic system/displacement device 130 to apply 2 newton of force on the tissue region. In another example, the displacement module 165 instructs the mechatronic system/displacement device 130 to cause a displacement of 4 mm to the tissue region. In one embodiment, the displacement module 165 sends a communication to apply the mechanical perturbation in response to receiving a message from the impedance module 160. The received message may be indicative of the baseline impedance of the tissue region calculated by the impedance module 160.

The displacement module 165 is further configured to communicate with the displacement device 130 to retract the displacement device 130 and reverse the application of the mechanical perturbation. In one embodiment, the displacement module 165 retracts the displacement device 130 in response to receiving a message from the impedance module 160 that the CI has reached a steady state CI. In another embodiment, the displacement module 165 retracts the displacement device 130 in response to receiving a message from the impedance module 160 indicating the rate of change of slow CI. In such an embodiment, the displacement device 130 is retracted after the impedance module 160 determines that the rate of change of CI is less than the CI threshold and before the rate of change of CI reaches steady state CI.

The timing module 170 includes codes and routines for calculating a compression duration and a retraction duration. In one embodiment, the timing module 170 includes a set of instructions executable by the processor 185 to provide the functionality for calculating the compression duration and the retraction duration. In another embodiment, the timing module 170 is stored in the memory 190 and is accessible and executable by the processor 185. In either embodiment, the timing module 170 is adapted for communication and cooperation with the processor 185 and other modules of the hydration application 155.

The timing module 170 is configured to calculate the compression duration as the difference between a time instant at which the mechanical perturbation is applied to the tissue region and a time instant at which the CI reaches the steady state CI. In one embodiment, the timing module 170 is further configured to calculate a fast compression duration and a slow compression duration. In such an embodiment, the timing module 170 calculates the fast compression duration as the difference between a time instant at which the mechanical perturbation is applied to the tissue region and a time instant at which the rate of change of CI is less than the CI threshold. The timing module 170 calculates the slow compression duration as the difference between a time instant at which the rate of change of CI is less than the CI threshold and a time instant at which the CI reaches steady state CI.

The timing module 170 is further configured to calculate the retraction duration as the difference between a time instant at which the displacement device 130 is retracted from the tissue region and a time instant at which the RI reaches the steady state RI. In one embodiment, the timing module 170 is further configured to calculate a fast retraction duration and a slow retraction duration. In such an embodiment, the timing module 170 calculates the fast retraction duration as the difference between a time instant at which the displacement device 130 is retracted from the tissue region and a time instant at which the rate of change of RI is less than the RI threshold. The timing module 170 calculates the slow retraction duration as the difference between a time instant at which the rate of change of RI is less than the RI threshold and a time instant at which the RI reaches steady state RI. The timing module 170 is further configured to send the calculated compression duration, the fast compression duration, the slow compression duration, the retraction duration, the fast retraction duration, and the slow retraction duration to the staging module 175.

The staging module 175 includes codes and routines for determining a hydration level of a tissue region. In one embodiment, the staging module 175 includes a set of instructions executable by the processor 185 to provide the functionality for determining the hydration level of the tissue region. In another embodiment, the staging module 175 is stored in the memory 190 and is accessible and executable by the processor 185. In either embodiment, the staging module 175 is adapted for communication and cooperation with the processor 185 and other modules of the hydration application 155.

The staging module 175 receives the rate of change of CI, the CI change, the fast CI change, the slow CI change, the rate of change of RI, the RI change, the fast RI change, and the slow RI change from the impedance module 160. The staging module 175 also receives the compression duration, the fast compression duration, the slow compression duration, the retraction duration, the fast retraction duration, and the slow retraction duration from the timing module 170. The staging module 175 determines a hydration level of the tissue region based on the aforementioned information received from the impedance module 160 and the timing module 170.

In one embodiment, the staging module 175 calculates a displacement depth of the tissue region based on at least one of the CI change, the fast CI change, the slow CI change, the RI change, the fast RI change, and the slow RI change. The displacement depth of the tissue region is the depth by which the tissue region gets indented due to the application of the mechanical perturbation. For example, the staging module 175 calculates the displacement depth of the tissue region as 2 mm if the magnitude of the CI change is 8 milliohms. In another example, the staging module 175 calculates the displacement depth as 5 mm if the magnitude of RI change is 15 milliohms. In another embodiment, in which the displacement module 165 applies the mechanical perturbation based on a pre-determined displacement, the staging module 175 determines the pre-determined displacement as the displacement depth.

In one embodiment, the staging module 175 determines the hydration level of the tissue region based on the calculated displacement depth. For example, the staging module 175 determines that the tissue region has stage-1 edema if the displacement depth is less than 2 mm. In another example, the staging module 175 determines that the tissue region has stage-2 edema if the displacement depth is 4 mm. In yet another example, the staging module 175 determines that the tissue region has stage-3 edema if the displacement depth is 6 mm. In yet another example, the staging module 175 determines that the tissue region has stage-4 edema if the displacement depth is 8 mm.

In another embodiment, the staging module 175 determines the hydration level of the tissue region based on at least one of the compression duration, the fast compression duration, the slow compression duration, the retraction duration, the fast retraction duration, and the slow retraction duration. For example, the staging module 175 determines that the tissue region has stage-1 edema if the retraction duration is less than 10 seconds. In another example, the staging module 175 determines that the tissue region has stage-2 edema if the retraction duration is within 10-15 seconds. In yet another example, the staging module 175 determines that the tissue region has stage-3 edema if the retraction duration is within 15-60 seconds. In yet another example, the staging module 175 determines that the tissue region has stage-4 edema if the retraction duration is within 1-5 minutes. In a further embodiment, the staging module 175 determines the hydration level of the tissue region based on a total duration. The staging module 175 calculates the total duration as the sum of the compression duration and the retraction duration.

In yet another embodiment, the staging module 175 determines the hydration level of the tissue region based on at least one of the rate of change of CI and the rate of change RI. In a further embodiment, the staging module 175 determines the hydration level of the tissue region based on either the rate of change of the slow CI or the rate of change of slow RI. For example, if the rate of change of slow RI is 15 milliohms/sec the staging module 175 determines that the tissue region has stage-1 edema. In another example, if the rate of change of slow RI is 3 milliohms/sec the staging module 175 determines that the tissue region has stage-3 edema.

Although the staging module 175 is described determining an edema stage (i.e., a stage of excess fluid in the tissue region) according to some embodiments, in other embodiments, the staging module 175 may determine a dehydration stage (i.e., a stage of less fluid in the tissue region) of the tissue region. For example, if the displacement depth is 0.1 mm and the retraction duration is 0.2 milliseconds, the staging module 175 determines that the tissue region has stage-3/severe dehydration. In another example, if the displacement depth is 1.1 mm and the retraction duration is 0.9 milliseconds, the staging module 175 determines that the tissue region has stage-1/mild dehydration. In any of the aforementioned embodiments, the staging module 175 sends the determined hydration level to the notification module 180. It should be noted that the various values and the associated stages discussed herein are examples and should not be construed as limiting the scope of the invention.

The notification module 180 includes codes and routines for generating and sending a notification to, for example, the user 110 or an administrator of the hydration monitoring device 150. In one embodiment, the notification module 180 includes a set of instructions executable by the processor 185 to provide the functionality for generating and sending the notification to the user 110 or an administrator of the hydration monitoring device 150. In another embodiment, the notification module 180 is stored in the memory 190 and is accessible and executable by the processor 185. In either embodiment, the notification module 180 is adapted for communication and cooperation with the processor 185 and the other modules of the hydration application 155.

The notification module 180 receives data from the staging module 175, generates a notification, and sends the notification to the user 110 and/or an administrator of the hydration monitoring device 150. The notification includes, for example, a graphical user interface displayed on a display (not shown) coupled to the hydration monitoring device 150, an e-mail, an alarm, a voice message, a short messaging service (SMS), and the like.

In one embodiment, the notification module 180 receives the durations calculated by the timing module 170 and the displacement depth from the staging module 175. The notification module 180 generates a notification including the displacement depth and the duration and sends it to an administrator (e.g., a nurse) for determining the hydration level. In a further embodiment, the notification module 180 also receives the hydration level of the tissue region from the staging module 175. The notification module 180 generates a notification including the hydration level of the tissue region and sends the notification to the user 110. In another embodiment, the notification module 180 generates and sends the notification based on the determined hydration level of the tissue region. For example, if the hydration level of the tissue region is determined as stage-1 edema or stage-2 edema, the notification module 180 generates and sends the notification to the user 110. In another example, if the hydration level of the tissue region is diagnosed as stage-3 edema or stage-4 edema, the notification module 180 sends the notification to the user 110 and a doctor who may be at a different location than the user 110.

Figure 2:
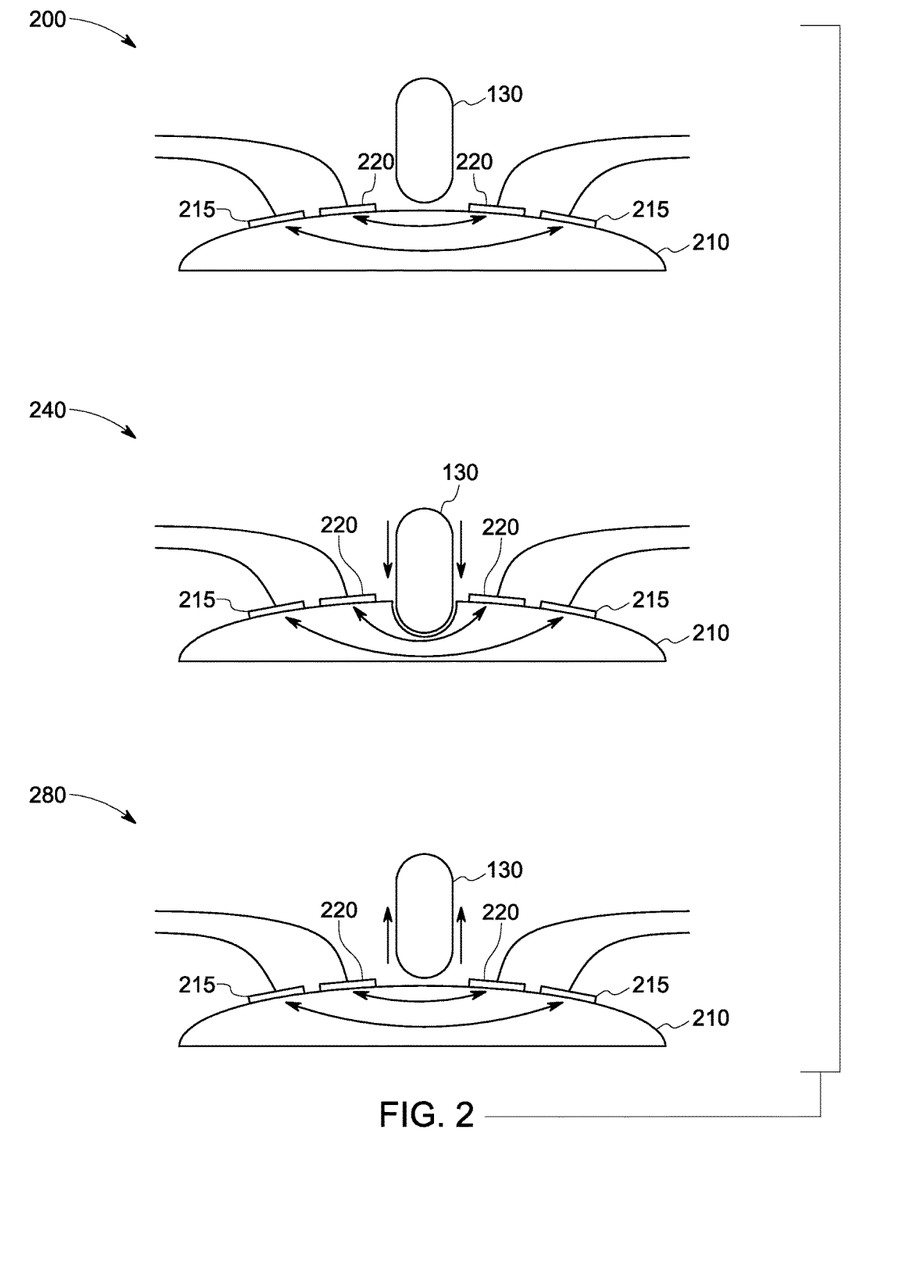
FIG. 2 is a diagrammatical representation of different stages for determining a hydration level of a tissue region according to one embodiment.

FIG. 2 is a diagrammatical representation of different stages 200, 240, 280 in the diagnosis of a tissue region according to one embodiment. In the illustrated embodiment, the stages 200, 240, 280 include diagrammatical representations of the displacement device 130, a tissue region 210, a pair of injection electrodes 215, and a pair of measurement electrodes 220. The pairs of injection electrodes 215 and the measurement electrodes 220 are disposed on top of the tissue region 210. The stage 200 illustrates the position of the displacement device 130 prior to the application of the mechanical perturbation on the tissue region 210. The impedance module calculates the baseline impedance of the tissue region 210 during the stage 200.

The stage 240 illustrates the application of mechanical perturbation on the tissue region 210. During the stage 240, the displacement device 130 receives a communication from the displacement module and pushes into the tissue region 210 to cause an indentation. During the stage 240, the hydration application calculates the CI, the rate of change of CI, the CI change, compression duration, and the like. The stage 280 illustrates the retraction of the displacement device 130 from the tissue region 210. During the stage 280, the displacement device 130 receives another communication from the displacement module to reverse the applied mechanical perturbation and retract from the tissue region 210. During the stage 280, the impedance module calculates the RI, the rate of change of RI, the RI change, retraction duration, and the like.

Figure 3:
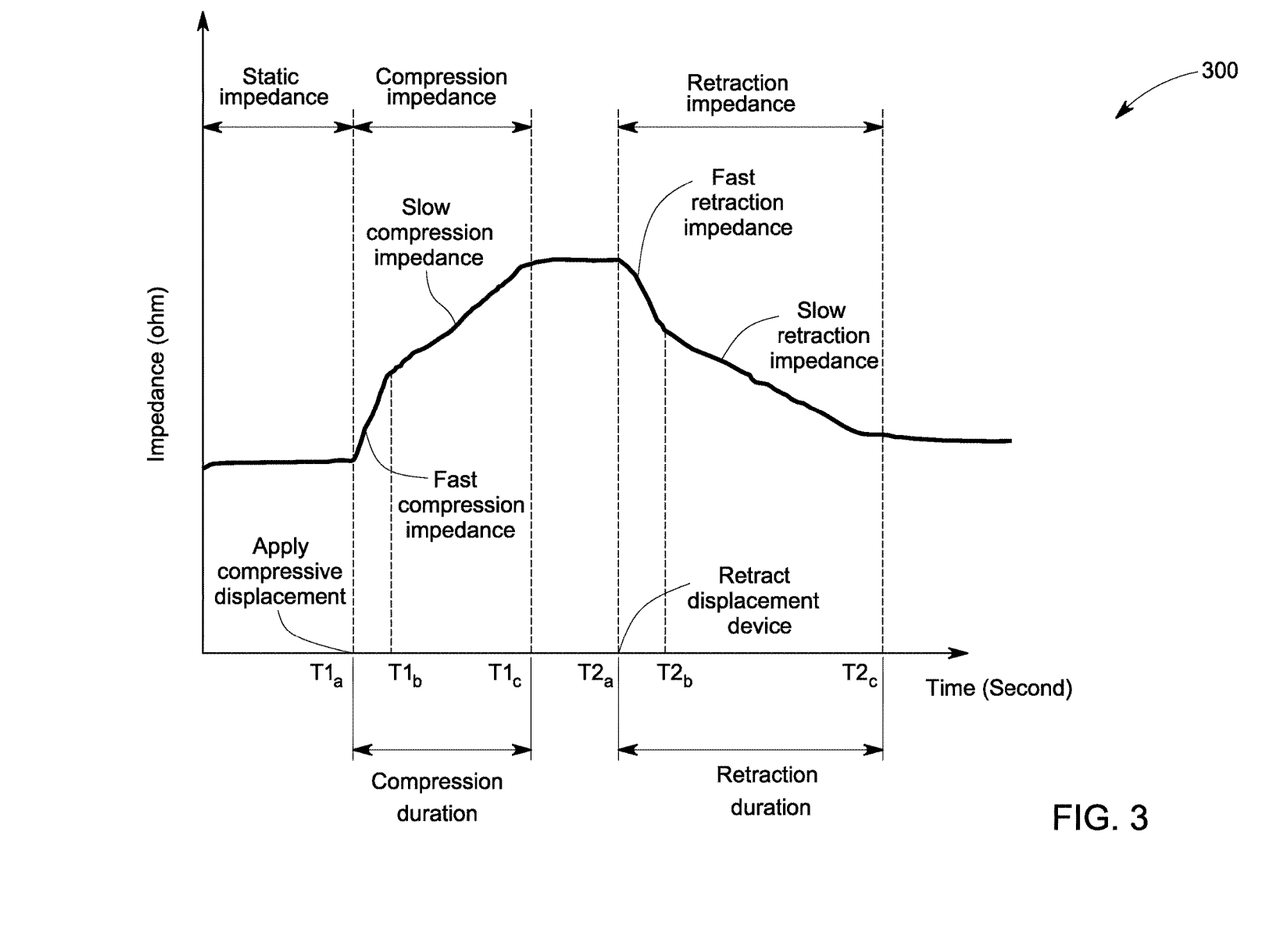
FIG. 3 is a graph depicting the impedance changes of a tissue region according to one embodiment.

FIG. 3 is a graph 300 depicting the impedance of the tissue region according to one embodiment. In the illustrated graph 300, the x-axis is represented by time (expressed in seconds) and the y-axis is represented by the impedance (expressed in ohms) of the tissue region calculated by the impedance module. The impedance module calculates the baseline impedance of the tissue region prior to the application of the mechanical perturbation (i.e., prior to time $T_{1a}$). At time $T_{1a}$, the displacement module sends a communication to the displacement device for applying a mechanical perturbation to the tissue region. The impedance module calculates the CI of the tissue region in response to the application of the mechanical perturbation.

In the illustrated embodiment, the impedance module determines that the rate of change of CI reaches steady state CI (i.e., within the stabilization threshold range) time $T_{1c}$. Thus, the impedance module calculates the CI change as the difference between the baseline impedance and the impedance value at time $T_{1c}$. Additionally, the timing module calculates the compression duration as the difference between $T_{1a}$ and $T_{1c}$. The impedance module also determines that the rate of change of CI is less than the CI threshold at time $T_{1b}$. The impedance module calculates the fast CI change as the difference between the baseline impedance and the impedance value at time $T_{1b}$. The impedance module further calculates the slow CI change as the difference between the impedance value at time $T_{1b}$ and the steady state CI. Additionally, the timing module calculates the fast compression duration as the difference between $T_{1a}$ and $T_{1b}$ and the slow compression duration as the difference between $T_{1b}$ and $T_{1c}$.

In the illustrated embodiment, at the time $T_{2a}$, the displacement module sends a communication for retracting the displacement device from the tissue region. The impedance module calculates the RI of the tissue region in response to retraction of the displacement device. The impedance module further determines that the rate of change RI has reached steady state RI (i.e., within the stabilization threshold range) at time $T_{2c}$. Thus, the impedance module calculates the RI change as the difference between the impedance value at time $T_{2a}$ and the steady state RI. Additionally, the timing module calculates the retraction duration as the difference between $T_{2a}$ and $T_{2c}$. The impedance module also determines that the rate of change of RI is less than the RI threshold at time $T_{2b}$. The impedance module calculates the fast CI change as the difference between the impedance value at time $T_{2a}$ and the impedance value at time $T_{2b}$. The impedance module further calculates the slow RI change as the difference between the impedance value at time $T_{2b}$ and the steady state RI. Additionally, the timing module calculates the fast retraction duration as the difference between $T_{2a}$ and $T_{2b}$ and the slow retraction duration as the difference between $T_{2b}$ and $T_{2c}$.

In the illustrated embodiment, although the displacement module retracts the displacement device after the CI reaches steady state CI, in other embodiments, the displacement module may retract the displacement device prior to the CI reaching steady state CI. For example, the displacement module retracts the displacement device once the impedance module calculates the rate of change slow CI. In such an embodiment, the staging module determines the hydration level of the tissue region based on, for example, rate of change of slow CI and the rate of change of slow RI.

Figure 4:
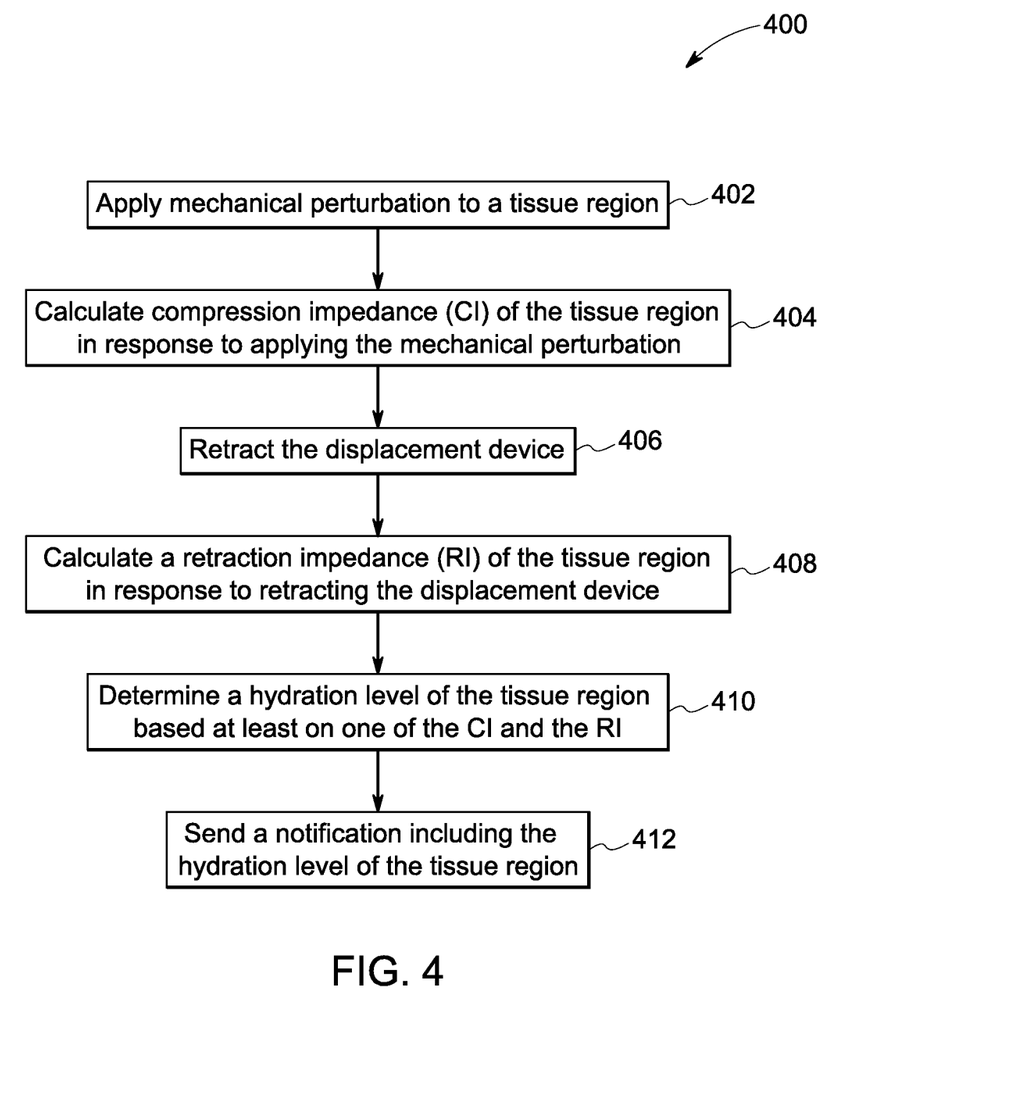
FIG. 4 is a flow diagrams illustrating a method for determining a hydration level of a tissue region according to one embodiment.

Referring now to FIG. 4, a flow diagram 400 of an exemplary method for determining a hydration level of a tissue region is illustrated. The displacement module applies a mechanical perturbation to a tissue region 402. For example, the displacement module sends a communication to a displacement device for causing an indentation to the tissue region based on a pre-determined force or a pre-determined displacement of the tissue region. The impedance module calculates a CI of the tissue region in response to applying the mechanical perturbation 404. The impedance module then retracts the displacement device 406. The impedance module calculates a RI of the tissue region in response to retracting the displacement device 408. The staging module then determines a hydration level of the tissue region based at least one of the CI and the RI 410. For example, the staging module determines an edema stage of the tissue region based on a rate of change of the CI and a rate of change of the RI. The notification module then sends a notification including the hydration level of the tissue region 412. For example, the notification module generates graphical user interface including the determined hydration level and sends it to a doctor.

Figure 5:
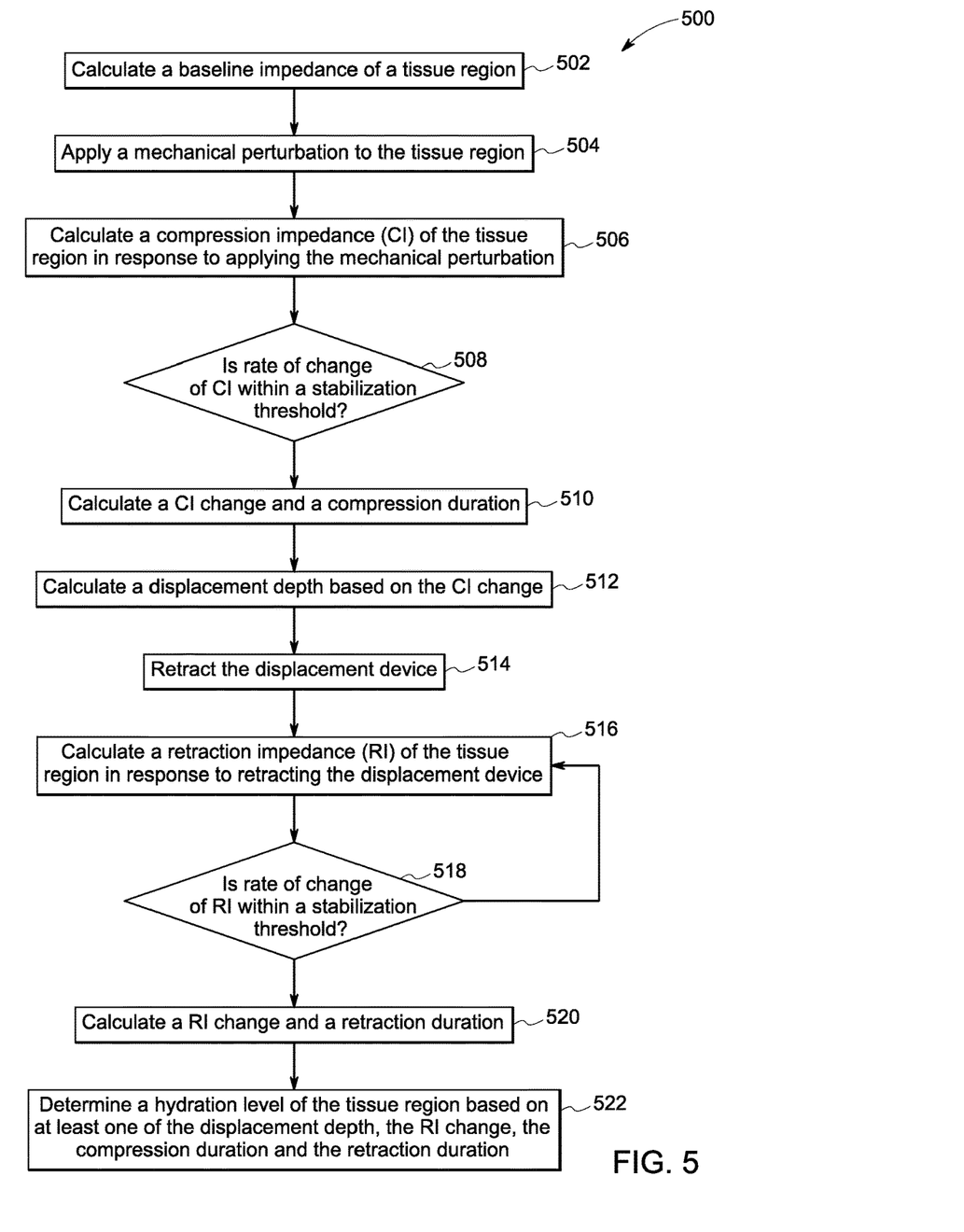
FIG. 5 is a flow diagram illustrating a method for determining a hydration level of a tissue region according to another embodiment.

Referring now to FIG. 5, a flow diagram 500 of another exemplary method for determining a hydration level of a tissue region is illustrated. The impedance module calculates a baseline impedance of a tissue region 502. The displacement module applies a mechanical perturbation to the tissue region 504. The impedance module calculates a CI of the tissue region in response to applying the mechanical perturbation 506. The impedance module then determines whether the rate of change of CI is within a stabilization threshold range 508. For example, the impedance module determines whether the rate of change of CI is within −0.5 milliohms/sec to +0.5 milliohms/sec to determine if the CI has reached a steady state CI. If the rate of change of CI is within the stabilization threshold range, the impedance module calculates the CI change and the timing module calculates the compression duration 510. The staging module further calculates the displacement depth based on the CI change 512.

The displacement module then retracts the displacement device 514. The impedance module calculates a RI of the tissue region in response to retracting the displacement device 516. The impedance module then determines if the rate of change of RI is within the stabilization threshold range 518. For example, the impedance module determines whether the rate of change of RI is within −0.5 milliohms/sec to +0.5 milliohms/sec to determine if the RI has reached a steady state RI. If the rate of change of RI is within the stabilization threshold range, the impedance module calculates the RI change and the timing module calculates the retraction duration 520. The staging module then calculates a hydration level of the tissue region based on at least one of the displacement depth, the RI change, the compression duration, and the retraction duration.

Figure 6A:
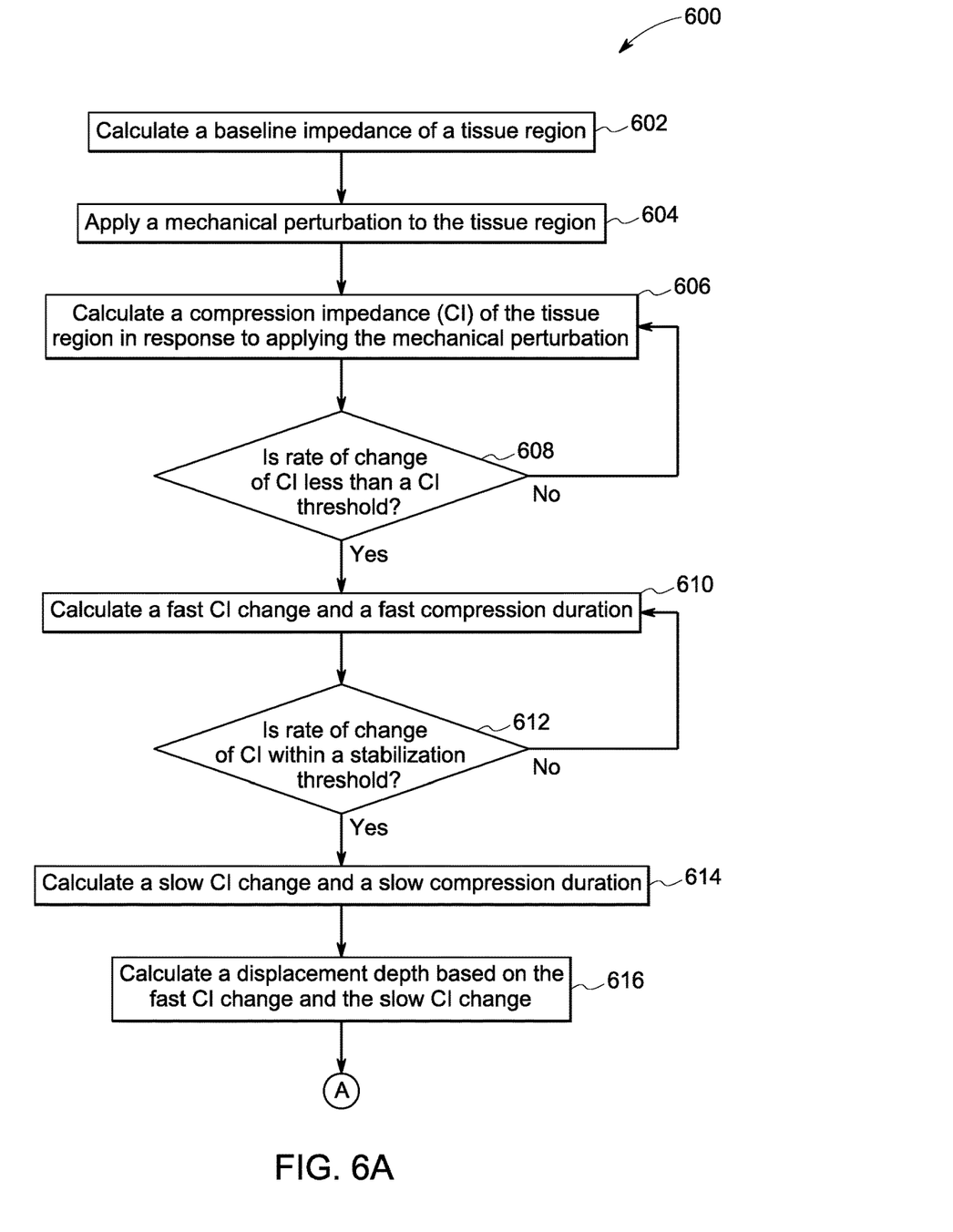
FIG. 6A is a flow diagram illustrating a method for determining a hydration level of a tissue region according to another embodiment.

Referring now to FIG. 6A, a flow diagram 600 of another exemplary method for determining a hydration level of a tissue region is illustrated. The impedance module calculates a baseline impedance of a tissue region 602. The displacement module applies a mechanical perturbation to the tissue region 604. The impedance module calculates a CI of the tissue region in response to applying the mechanical perturbation 606. The impedance module then determines whether the rate of change of CI is less than a CI threshold 608. For example, the impedance module determines whether the rate of change of CI is less than 2 ohms/second. If the rate of change of CI is less than the CI threshold, the impedance module calculates a fast CI change and the timing module calculates a fast compression duration 610. The impedance module then determines whether the rate of change of CI is within a stabilization threshold range 612. If the rate of change of CI is within the stabilization threshold range, the impedance module calculates the slow CI change and the timing module calculates the slow compression duration 614. The staging module further calculates the displacement depth based on the fast CI change and the slow CI change 616.

Figure 6B:
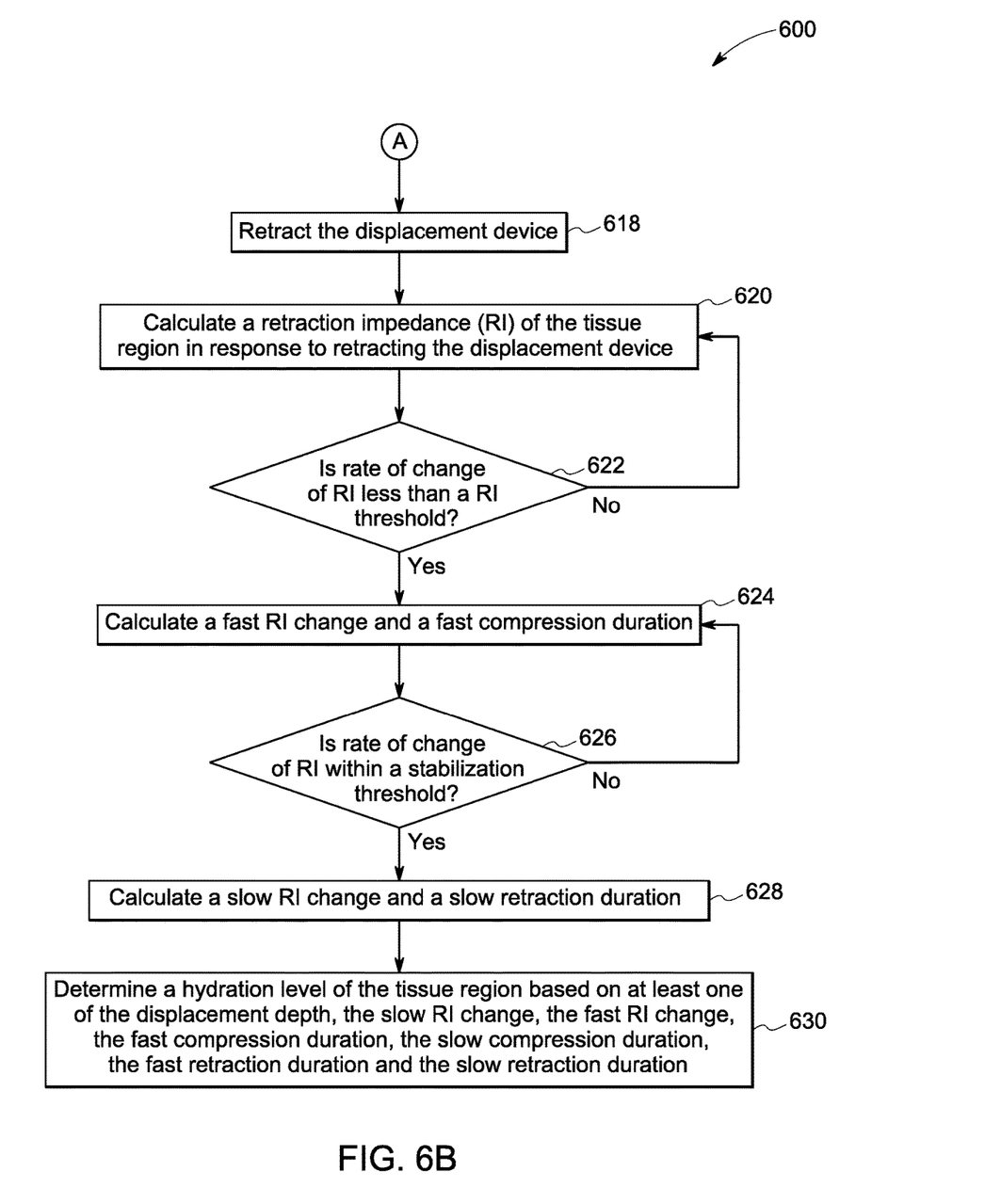
FIG. 6B is a flow diagram illustrating a method for determining a hydration level of a tissue region in accordance with the exemplary embodiment of FIG. 6A.

Referring now to FIG. 6B, the remaining steps of the flow diagram 600 for determining a hydration level of a tissue region is illustrated. The displacement module retracts the displacement device 618. The impedance module calculates a RI of the tissue region in response to retracting the displacement device 620. The impedance module then determines whether the rate of change of RI is less than a RI threshold 622. If the rate of change of RI is less than the RI threshold, the impedance module calculates a fast RI change and the timing module calculates a fast retraction duration 624. The impedance module then determines whether the rate of change of RI is within a stabilization threshold range 626. If the rate of change of RI is within the stabilization threshold range, the impedance module calculates the slow RI change and the timing module calculates the slow retraction duration 628. The staging module determines a hydration level of the tissue region based on at least one of the displacement depth, the slow RI change, the fast RI change, the fast compression duration, the slow compression duration, the fast retraction duration and the slow retraction duration 630.

Figure 7:
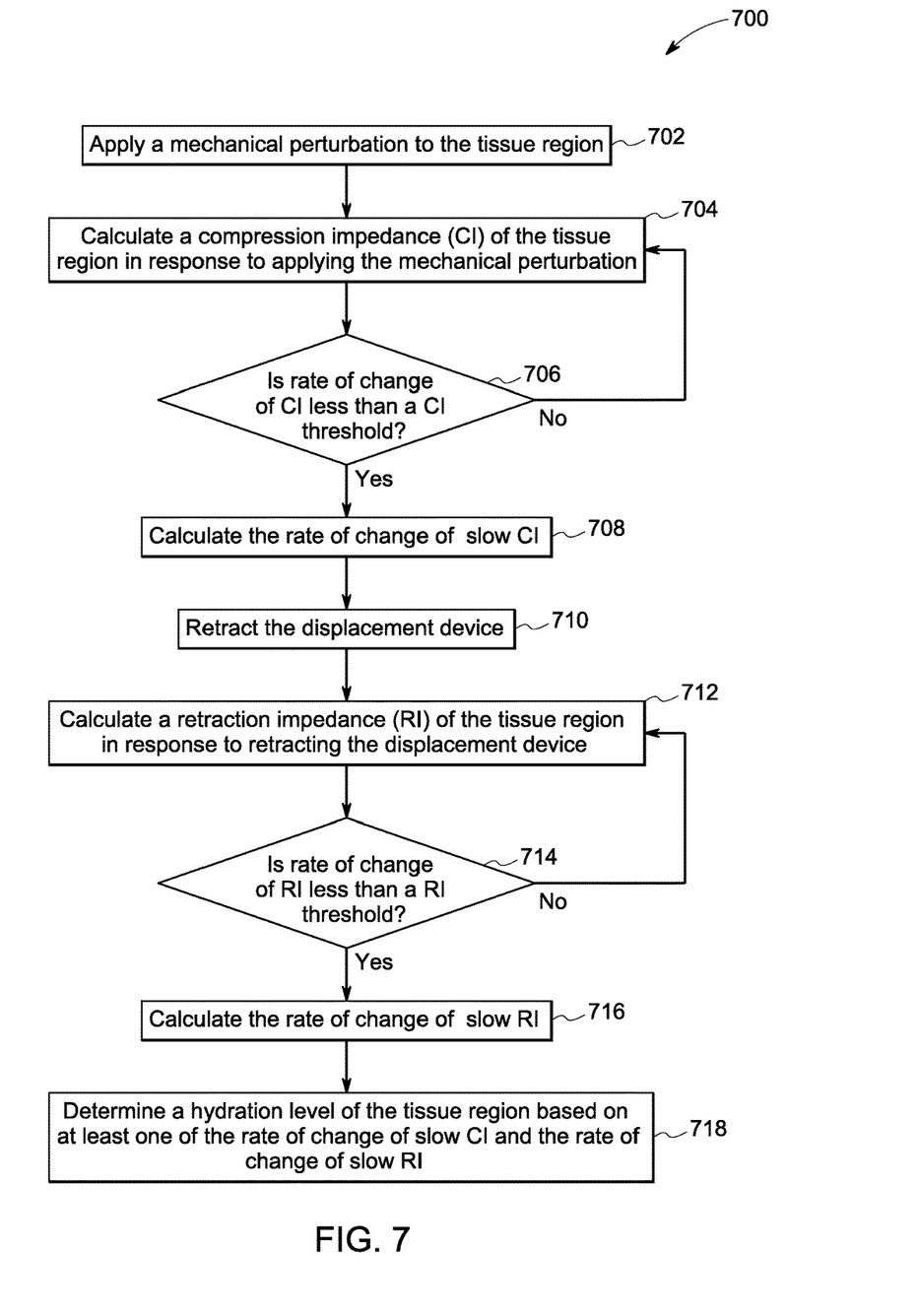
FIG. 7 is a flow diagram illustrating a method for determining a hydration level of a tissue region according to another embodiment.

Referring now to FIG. 7, a flow diagram 700 of another exemplary method for determining a hydration level of a tissue region is illustrated. The displacement module applies a mechanical perturbation to the tissue region 702. The impedance module calculates a CI of the tissue region in response to applying the mechanical perturbation 704. The impedance module then determines whether the rate of change of CI is less than a CI threshold 706. If the rate of change of CI is less than the CI threshold, the impedance module further calculates a rate of change of the slow CI 708. The displacement module then retracts the displacement device 710. The impedance module calculates a RI of the tissue region in response to retracting the displacement device 712. The impedance module then determines whether the rate of change of RI is less than a RI threshold 714. If the rate of change of RI is less than the RI threshold, the impedance module further calculates a rate of change of the slow RI 716. The staging module then determines a hydration level of the tissue region based on at least one of the rate of change of slow CI and the rate of change of slow RI 718. Since the hydration level is determined based on the rate of change of slow CI and slow RI, the displacement module does not have to wait until the CI reaches a steady state CI for retracting the displacement device.

The above described system and method of determining a hydration level of a tissue region based on impedance measurements is advantageous as it is accurate and quantitative compared to the conventional qualitative and subjective methods practiced by physicians. Additionally, the hydration monitoring device enables a user (e.g., homecare patient) to determine the hydration level at home and avoid expensive visits to a hospital.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the system can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A method comprising:
    applying an electric current, via a plurality of electrodes disposed on top of a tissue region, to the tissue region and measuring an electric voltage across the tissue region generated due to the electric current;
    applying an indentation to the tissue region using a displacement device positioned such that the indentation is solely applied in-between the plurality of electrodes;
    calculating, by an impedance module, a compression impedance (CI) of the tissue region in response to applying the indentation based on the applied electric current and the measured electric voltage;
    retracting the displacement device;
    calculating, by the impedance module, a retraction impedance (RI) of the tissue region in response to retracting the displacement device based on the applied electric current and the measured electric voltage;
    determining, by the impedance module, at least one of a change in the CI and a change in the RI based on a stabilization threshold range, the CI, and the RI; and
    determining, by a staging module, a hydration level of the tissue region based at least on one of the change in the CI and the change in the RI.

2. The method of claim 1, wherein the hydration level includes at least one of an edema stage and a dehydration stage of the tissue region.

3. The method of claim 1, further comprising applying the indentation to the tissue region based on at least one of a pre-determined force and a pre-determined displacement of the tissue region.

4. The method of claim 1, further comprising:
    calculating a rate of change of the CI and a rate of change of the RI based on at least one of a linear function, a quadratic function, and an exponential function; and
    determining the hydration level of the tissue region based on at least one of the rate of change of the CI and the rate of change of the RI, wherein the rate of change of the CI and the rate of change of the RI correspond to application of the indentation, and retraction of the displacement device from the tissue region respectively.

5. The method of claim 4, wherein determining at least one of the change in the CI and the change in the RI comprises:
    determining whether the rate of change of the CI is within the stabilization threshold range;
    calculating the change in the CI in response to determining that the rate of change of the CI is within the stabilization threshold range; and
    determining the hydration level of the tissue region based on the change in the CI, wherein the change in the CI is a difference between a baseline impedance and a steady state CI.

6. The method of claim 5, further comprising:
calculating a compression duration in response to determining that the rate of change of the CI is within the stabilization threshold range; and
determining the hydration level of the tissue region based on the compression duration.

7. The method of claim 5, wherein the change in the CI further comprises a slow CI change and a fast CI change, and wherein the slow CI change is caused due to compression of fluid in the tissue region and the first CI change is caused due to compression of skin in the tissue region.

8. The method of claim 5, further comprising retracting the displacement device in response to determining that the rate of change of the CI is within the stabilization threshold range.

9. The method of claim 8, wherein determining at least one of the change in the CI and the change in the RI comprises:
determining whether the rate of change of the RI is within the stabilization threshold range;
calculating the change in the RI in response to determining that the rate of change of the RI is within the stabilization threshold range; and
determining the hydration level of the tissue region based on the change in the RI, wherein the change in the RI is a difference between the steady state CI and a steady state RI.

10. The method, of claim 9, further comprising:
calculating a retraction duration in response to determining that the rate of change of the RI is within the stabilization threshold range; and
determining the hydration level of the tissue region based on the retraction duration.

11. The method of claim 9, wherein the change in the RI further comprises a slow RI change and a fast RI change, and wherein the slow RI change is caused due to expansion of fluid in the tissue region and the fast RI change is caused due to expansion of skin in the tissue region.

12. A system comprising:
at least one processor;
a plurality of electrodes disposed on top of a tissue region configured to apply an electric current to the tissue region and measure an electric voltage across the tissue region generated due to the electric current;
a displacement module stored in a memory and executable by the at least one processor, the displacement module for applying an indentation to the tissue region using a displacement device positioned such that the indentation is solely applied in-between the plurality of electrodes and retracting the displacement device;
an impedance module stored in the memory and executable by the at least one processor, the impedance module communicatively coupled to the displacement module for calculating a compression impedance (CI) of the tissue region in response to applying the indentation based on the applied electric current and the measured electric voltage, calculating a retraction impedance (RI) of the tissue region in response to retracting the displacement device based on the applied electric current and the measured electric voltage, and determining at least one of a change in the CI and a change in the RI based on a stabilization threshold range, the CI, and the RI; and, a staging module stored in the memory and executable by the at least one processor, the staging module communicatively coupled to the impedance module for determining a hydration level of the tissue region based at least on one of the change in the CI and the change in the RI.

13. The system of claim 12, wherein the hydration level includes at least one of an edema stage and a dehydration stage of the tissue region.

14. The system of claim 12, wherein the impedance module further calculates a rate of change of the CI and a rate of change of the RI based on at least one of a linear function, a quadratic function, and an exponential function, and wherein the rate of change of the CI and the rate of change of the RI correspond to application of the indentation, and retraction of the displacement device from the tissue region respectively.

15. The system of claim 14, wherein the impedance module further determines whether the rate of change of the CI is within the stabilization threshold range, calculates the change in the CI in response to determining that the rate of change of the CI is within the stabilization threshold range, determines whether the rate of change of RI is within the stabilization threshold range, and calculates a change in RI in response to determining that the rate of change of the RI is within the stabilization threshold range, wherein the change in the CI is a difference between a baseline impedance and a steady state CI, and wherein the change in the RI is a difference between the steady state CI and a steady state RI.

16. The system of claim 15, wherein the change in the CI comprises a slow CI change and a fast CI change and the change in the RI includes a slow RI change and a Bast RI change, wherein the slow CI change is caused due to compression of fluid in the tissue region, and the fast CI change is caused due to compression of skin in the tissue region, and wherein the slow RI change is caused due to, expansion of fluid in the tissue region and the fast RI change is caused due to expansion of skin in the tissue region.

17. The system of claim 15, wherein the displacement module retracts the displacement device in response to determining that the rate of change of the CI is within the stabilization threshold range.

18. The system of claim 15, further comprising a timing module for calculating a compression duration in response to determining that the rate of change of the CI is within the stabilization threshold range and calculating a retraction duration in response to determining that the rate of change of the RI is within the stabilization threshold range.

19. The system of claim 15, wherein the staging module further determines the hydration level based on at least one of the rate of change of the CI, the rate of change of the RI, the change in the CI, or the change in the RI.

20. A computer program product comprising a non-transitory computer readable medium encoding instructions that, in response to execution by at least one processor, cause the processor to perform operations comprising:
applying an electric current, via a plurality of electrodes disposed on top, of a tissue region, to the tissue region and measuring an electric voltage across the tissue region generated due to the electric current;
applying an indentation to the tissue region using a displacement device positioned such that the indentation is solely applied in-between the plurality of electrodes;
calculating, by an impedance module, a compression impedance (CI) of the tissue region in response to applying the indentation based on the applied electric current and the measured electric voltage;
retracting the displacement device;

calculating, by the impedance module, a retraction impedance (RI) of the tissue region in response to retracting the displacement device based on the applied electric current and the measured electric voltage;
determining, by the impedance module, at least one of a change in the CI and a change in, the RI based on a stabilization threshold range, the CI and the RI; and
determining, by a staging module, a hydration level of the tissue region based on at least one of the change in the CI and the change in the RI.

* * * * *